(12) United States Patent
Shapley et al.

(10) Patent No.: US 10,272,200 B2
(45) Date of Patent: Apr. 30, 2019

(54) MANAGING COMMUNICATIONS TO AND FROM A HANDSET DEVICE CONTROLLING A THERAPEUTIC PRODUCT DELIVERY DEVICE

(71) Applicant: Cellnovo Limited, Swansea (GB)

(72) Inventors: Julian Shapley, Swansea (GB); Matthew Powell, Swansea (GB); Anthony Martin, Swansea (GB); Mark Jones, Swansea (GB)

(73) Assignee: Cellnovo Limited, Swansea (GB)

( * ) Notice: Subject to any disclaimer, the term of this patent is extended or adjusted under 35 U.S.C. 154(b) by 0 days.

(21) Appl. No.: 15/114,834

(22) PCT Filed: Jan. 30, 2015

(86) PCT No.: PCT/GB2015/050250
§ 371 (c)(1),
(2) Date: Jul. 27, 2016

(87) PCT Pub. No.: WO2015/114372
PCT Pub. Date: Aug. 6, 2015

(65) Prior Publication Data
US 2016/0339176 A1    Nov. 24, 2016

(30) Foreign Application Priority Data

Jan. 30, 2014   (GB) .................................. 1401589.5

(51) Int. Cl.
*A61M 5/172*   (2006.01)
*H04W 4/70*    (2018.01)
(Continued)

(52) U.S. Cl.
CPC .......... *A61M 5/1723* (2013.01); *A61B 5/002* (2013.01); *A61B 5/0022* (2013.01);
(Continued)

(58) Field of Classification Search
CPC ............... G06F 19/3418; G06F 19/322; G06F 19/3487; G06F 19/345; G06Q 50/22;
(Continued)

(56) References Cited

U.S. PATENT DOCUMENTS 5,867,688 A    2/1999   Simmon et al.
6,381,029 B1 *  4/2002   Tipirneni ............... G06F 19/321
                                                  358/1.14

(Continued)

FOREIGN PATENT DOCUMENTS

CN    201134101    10/2008
EP      1839694    10/2007
(Continued)

OTHER PUBLICATIONS

3GPP TS 23.003 V10.0.0 Numbering, addressing and identification. Dec. 2010.*

(Continued)

*Primary Examiner* — Julio R Perez
*Assistant Examiner* — Ernest G Tacsik
(74) *Attorney, Agent, or Firm* — Kang S. Lim (57) ABSTRACT

A communication method of managing communications to and from a handset device controlling a therapeutic product delivery device is described. The method comprises transmitting, to a server, at least part of a unique identifier for a handset device for controlling a therapeutic product delivery device, and patient information regarding a user to be associated with the handset device, and at the server, associating the handset device with the patient information, generating a handset specific code, and transmitting the handset specific code to the user. At the handset device, a manual input of the handset specific code is received, and the future transmission of data from the handset device to the server carried out in association with the handset specific (Continued)

code. In this way, the server can be sure that the user is in possession of the handset (because the user received the code via the secure portal, and was required to manually input it to the handset), and can therefore be confident that communications received in association with that code are associated with the correct user and handset.

13 Claims, 5 Drawing Sheets (51) Int. Cl.
*G06F 19/00* (2018.01)
*H04L 29/06* (2006.01)
*A61B 5/00* (2006.01)
*A61B 5/11* (2006.01)
*A61B 5/145* (2006.01)
*A61M 5/142* (2006.01)
*H04L 29/08* (2006.01)
*H04W 4/14* (2009.01)

(52) U.S. Cl.
CPC ........ *A61B 5/1118* (2013.01); *A61B 5/14532* (2013.01); *A61B 5/4839* (2013.01); *A61M 5/142* (2013.01); *G06F 19/00* (2013.01); *G06F 19/3418* (2013.01); *G06F 19/3468* (2013.01); *H04L 63/0876* (2013.01); *H04L 67/06* (2013.01); *H04L 67/1095* (2013.01); *H04W 4/14* (2013.01); *H04W 4/70* (2018.02); *A61M 2205/3389* (2013.01); *A61M 2205/3553* (2013.01); *A61M 2205/3569* (2013.01); *A61M 2230/005* (2013.01); *A61M 2230/201* (2013.01)

(58) Field of Classification Search
CPC ...... G06Q 50/24; G06Q 20/32; A61B 5/0022; A61B 5/0002; H04W 12/06; A61M 5/1723; A61M 2230/201; A61M 5/14244
See application file for complete search history.

(56) References Cited

U.S. PATENT DOCUMENTS

| 8,285,487 | B2 | 10/2012 | Bergstrom et al. |
| 2005/0055242 | A1 | 3/2005 | Bello et al. |
| 2007/0078784 | A1 | 4/2007 | Donovan et al. |
| 2007/0179885 | A1* | 8/2007 | Bird ........................ G06Q 20/04 705/39 |
| 2007/0233051 | A1 | 10/2007 | Hohl et al. |
| 2009/0063193 | A1 | 3/2009 | Barton et al. |
| 2010/0076275 | A1* | 3/2010 | Chu ..................... G06F 19/363 600/300 |
| 2010/0137784 | A1 | 6/2010 | Cefai et al. |
| 2010/0286997 | A1 | 11/2010 | Srinivasan |
| 2011/0225024 | A1* | 9/2011 | Seyer ..................... G07C 13/00 705/12 |
| 2011/0246235 | A1* | 10/2011 | Powell ................... G06Q 10/10 705/3 |
| 2011/0316562 | A1 | 12/2011 | Cefai et al. |
| 2012/0054841 | A1* | 3/2012 | Schultz .................. G06F 21/44 726/6 |
| 2012/0182939 | A1 | 7/2012 | Rajan et al. |
| 2012/0232520 | A1* | 9/2012 | Sloan ................. A61B 5/14532 604/504 |
| 2013/0030841 | A1 | 1/2013 | Bergstrom et al. |
| 2013/0036100 | A1* | 2/2013 | Nagpal ............. G06F 17/30156 707/692 |
| 2013/0080832 | A1 | 3/2013 | Dean et al. |
| 2013/0173473 | A1 | 7/2013 | Birtwhistle et al. |

FOREIGN PATENT DOCUMENTS

| GB | 2443261 | 4/2008 |
| GB | 2495014 | 3/2013 |
| GB | 1401589.5 | 1/2014 |
| JP | 2007307359 | 11/2007 |
| JP | 2012210441 | 11/2012 |
| WO | WO 2005/031631 | 4/2005 |
| WO | WO 2007/112034 | 10/2007 |
| WO | WO 2009/023634 | 2/2009 |

OTHER PUBLICATIONS

U.K. Intellectual Property Office, GB Application No. GB 1401589. 5, "Search Report under Section 17" Jul. 27, 2015, 3 pages.
European Patent Office, "Notification of Transmittal of the ISR and the Written Opinion of the International Searching Authority, or the Declaration," in PCT Application No. PCT/GB2015/050250, dated May 7, 2015, 9 pages.
Korean Intellectual Property Office, Korean Patent Application No. 10-2016-7023323, Korean Office Action, dated Sep. 20, 2017 with transmittal letter dated Sep. 27, 2017 and English translation of Office Action rejections, 15 pages.

* cited by examiner

MANAGING COMMUNICATIONS TO AND FROM A HANDSET DEVICE CONTROLLING A THERAPEUTIC PRODUCT DELIVERY DEVICE

CROSS-REFERENCE TO RELATED APPLICATIONS

The present application is a United States National Stage entry under 35 U.S.C. § 371 of International Application No. PCT/GB2015/050250 filed Jan. 30, 2015, designating the United States of America and published in English on Aug. 6, 2015, which in turn claims priority to Great Britain Application No. 1401589.5, filed Jan. 30, 2014, each of which is incorporated herein by reference in their entirety.

FIELD OF THE INVENTION

The present invention relates to a method and system for managing communications to and from a handset device controlling a therapeutic product delivery device.

BACKGROUND TO THE INVENTION

Conventionally, Type 1 diabetes has been treated with daily insulin injections. However, this inevitably results in insulin levels that do not match the normal and rapid changes in blood glucose which occur in a patient throughout the day. On the one hand, insufficient insulin and high glucose levels lead to immediate symptoms and contribute to long-term complications. On the other hand, too much insulin may result in too little blood sugar leading to loss of consciousness and convulsions. As an alternative to injections, insulin pump therapy is intended to mimic the normal physiology of the healthy pancreas. Unlike multiple daily insulin injections, an insulin pump is able to provide a constant background infusion of insulin that can be adjusted according to individual need, compensating for daily activity and exercise routines. The pump may also be programmed to deliver bolus doses of insulin to address the big glucose swings in the blood that would otherwise result from eating and drinking. By mimicking the natural physiology of the pancreas, insulin pump therapy aims to maintain a constantly normal blood glucose level; avoiding the highs that are associated with meals or the lows that come from too much insulin.

The pump may be controlled wirelessly by a handset device. The handset device may record medical data regarding the patient, and it is desirable that the medical data be made available (synchronised to) a server, so that it can be accessed remotely by medical staff (for diagnostic purposes) and the service operator (to monitor device performance). Given the sensitivity of medical data, and regulatory constraints on where that data may be stored, and who may be provided with access to it, there are a number of unique problems associated with medical information acquired at the handset being communicated to a remote server.

SUMMARY OF THE INVENTION

According to an aspect of the present invention, there is provided a communication method of managing communications to and from a handset device controlling a therapeutic product delivery device, comprising the steps of:

transmitting, to a server, at least part of a unique identifier for a handset device for controlling a therapeutic product delivery device, and patient information regarding a user to be associated with the handset device;

at the server, associating the handset device with the patient information, generating a handset specific code, and transmitting the handset specific code to the user;

at the handset device, receiving a manual input of the handset specific code; and transmitting data from the handset device to the server in association with the handset specific code.

In this way, the server can be sure that the user is in possession of the handset (because the user received the code via the secure portal, and was required to manually input it to the handset), and can therefore be confident that communications received in association with that code are associated with the correct user and handset.

Preferably, the patient information comprises the user's country of residence, and the server is responsive to the receipt of the handset specific code to establish a routing to a medical data server associated with the patient's country of residence. In this way, regulations requiring medical data to be stored only in the country where a user is resident can be complied with. Preferably, the routing is established by providing the handset device with the IP address of the medical data server, and the handset device is operable to drop the connection to the server and reattach to the medical data server at the indicated IP address. In this way, the medical data itself need not even be provided to the global server in a transitory manner—the only connection to the global server may be request an IP address for routing the medical data to a permitted server. In this regard, the handset device may be operable to transmit medical data regarding the user to the medical data server.

Preferably, the server is responsive to the receipt of the handset specific code to provide customer support information to the handset device, and the handset device is responsive to receipt of the customer support information to update the customer support information for display at the handset. In this way, the customer support information can be kept up to date.

The unique identifier may be an International Mobile station Equipment Identity.

The medical data may comprise one or more of the activity of or settings for the therapeutic product delivery device, carbohydrate input information and blood glucose readings.

In some embodiments, the handset is automatically configured in dependence on the patient's country of residence.

The patient information may comprise a medical facility, clinic, healthcare professional or medical insurance company the user is associated with, and the handset may be automatically configured in dependence on the medical facility, clinic, healthcare professional or medical insurance company associated with the user.

In some embodiments, if the server identifies in response to the unique identifier that the handset device is already associated with another user, the server is operable to cancel the association between the handset device and the other user. This reduces the risk of a handset storing medical data regarding multiple users. The unique identifier for the handset device may be pre-stored at the server in advance of the patient information being transmitted to the server.

According to another aspect of the present invention, there is provided a system for managing communications to and from a handset device controlling a therapeutic product delivery device, the system comprising:

a server, for receiving at least part of the unique identifier for the handset device, and patient information regarding a user to be associated with the handset device, the server being operable to associate the handset device with the patient information, generate a handset specific code, and transmit the handset specific code to the user; and a handset device, for receiving a manual input of the handset specific code transmitting data from the handset device to the server in association with the handset specific code.

According to another aspect of the present invention, there is provided a communication method for managing communications to and from a handset device controlling a therapeutic product delivery device, comprising the steps of:

transmitting, to a server, at least part of a unique identifier for a handset device for controlling a therapeutic product delivery device, and communication information specifying whether or not data from the handset device is to be communicated to the server;

at the server, entering a data accepting state or a non-data accepting state in relation to the handset in response to the communication information, generating a handset code, and transmitting the handset code to the user;

at the handset device, receiving a manual input of the handset code and in response to the handset code entering a data transmitting state or a non-data transmitting state consistent with the communication information.

According to another aspect of the present invention, there is provided a communication method for managing communications to and from a handset device controlling a therapeutic product delivery device, comprising the steps of:

transmitting, to a server, at least part of a unique identifier for a handset device for controlling a therapeutic product delivery device, and an unassign request for the handset device;

at the server, in response to the unassign request, entering a non-data accepting state in relation to the handset, generating a handset code, and transmitting the handset code to the user;

at the handset device, receiving a manual input of the handset code and in response to the handset code erasing medical information relating to the user from the handset device.

Various other aspects and features of the present invention are described in the embodiments which follow.

DETAILED DESCRIPTION

The invention will now be described by way of example with reference to the following Figures in which.

System

Figure 1:
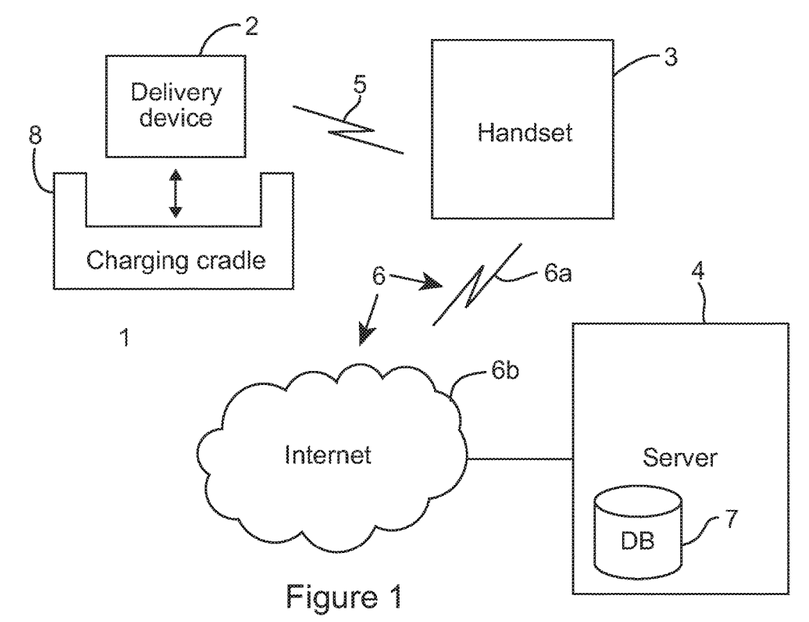
FIG. 1 shows a schematic view of a drug delivery system.

Referring to FIG. 1, a drug delivery system 1 is schematically illustrated. The drug delivery system 1 in this case delivers insulin to a patient. However, it will be appreciated that embodiments of the present invention may be appropriate for delivering drugs other than insulin. The system 1 comprises a delivery device 2 which is worn on the patient's body, a handset 3 (which may appear similar to a smartphone) for controlling the delivery device 2, and a server 4. The delivery device 2 and the handset 3 are able to communicate via a first wireless connection 5, for example a lower power ANT radio connection. The handset 3 and the server 4 are able to communicate via a second wireless connection 6, for example a GPRS mobile data connection 6a and the Internet 6b. The server 4 comprises a patient database 7 for storing patient medical information and other information about the patient. Both the delivery device 2 and the handset 3 are powered by rechargeable batteries. Also shown in FIG. 1 is a charging cradle 8 into which the delivery device 2 is inserted in order to charge the delivery device 2.

Delivery Device

Figure 2:
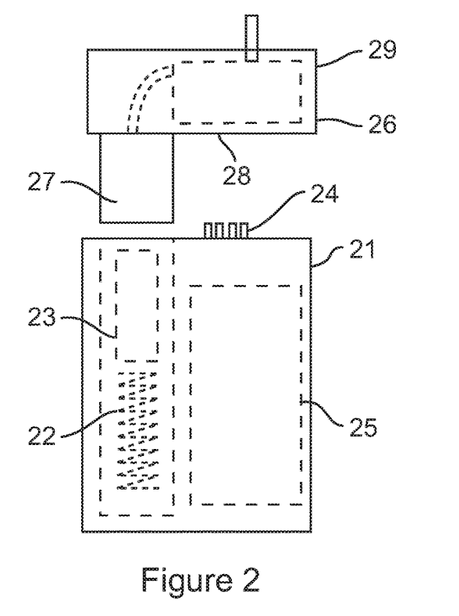
FIG. 2 shows a schematic view of a drug delivery device.

The delivery device comprises two parts, which are detachable from each other, as shown schematically in FIG. 2. The first of the two parts is a body 21, which contains a spring 22, a biasing member 23 including a displacement sensor (for example as described in US2011/0316562), and a set of contact pins 24 for providing an electrical connection with the second part. The body 21 also comprises a battery, control circuitry and a transceiver for communicating with the handset, which are not separately shown in FIG. 2 in the interests of clarity, but are generally represented by element 25. The second of the two parts is a disposable insulin cartridge 26, which comprises a reservoir 27 of insulin, contact pads 28 for providing an electrical connection with the body 21 via the pins 24, a pumping device (a wax actuator, for example as described in GB2443261) for pumping the insulin from the reservoir 27 into the patient's body, and a valve arrangement (for example as described in US2010/0137784). The pumping device and valve arrangement are not separately shown in FIG. 2 in the interests of clarity, but are generally represented by element 29. It will be understood that the body 21 of the delivery device is reusable, while the disposable cartridge 26 is intended to be removed and disposed of when the reservoir 27 has been depleted, or when the cartridge has passed its use by date, or if it develops a fault. A new cartridge can then be engaged with the body 21. While it is preferable that the cartridge is disposable, it will be appreciated that, in principle, the cartridge may be refilled and reused again rather than being disposed of. However, even in this case the cartridge should be removable from the body so that a new (full) cartridge can be used while the original cartridge is being refilled.

In use, the body 21 and the cartridge 26 of the delivery device 2 are physically and electrically connected. The electrical connection is via the pins 24 and pads 28. The physical connection may be provided by clips or any other releasable engagement mechanism (not shown). The control circuitry in the body 21 is responsive to control signals received from the handset 3 via the wireless connection 5 to draw current from the battery and apply an electrical current via the pins 24 and the pads 28 to activate the pumping device within the cartridge 26 to draw fluid from the reservoir 27 through the valve arrangement and out of the delivery device 2 to a patient's body. The rate of delivery of the therapeutic product can be controlled by the control circuitry to achieve a particular basal delivery rate, or bolus dose, by controlling the amount and timing of electrical current to the pumping device. Although the basal rate is set by the handset, once set the delivery device 2 is able to maintain the set basal rate with no further communication from the handset 3. As can be seen in FIG. 2, when the body 21 and the cartridge 26 are in engagement, the reservoir 27 is received within the body 21, displacing the biasing member (and displacement sensor) 23 and compressing the spring 22. The compressed spring applies a biasing force to a base of the reservoir 27 via the biasing member 23. The biasing force does not in isolation force insulin from the reservoir 27 through the valve arrangement and into the patient's body, but when combined with the pumping action of the pumping device, the biasing force pressurises the insulin in the reservoir 27 to refill a pumping chamber in advance of each pumping action. It is the pumping action which drives a controlled amount of insulin from the pumping chamber through an outlet valve and to the patient's body. The reservoir takes the form of a cylinder having a first end from which insulin is drawn under the action of the pump, and a second end opposite to the first end at which the (moveable) base is provided. The base of the reservoir moves inwardly of the reservoir (to effectively decrease the size of the reservoir) as the insulin is pumped from the reservoir, under the biasing force provided by the biasing member 23. The position of the biasing member 23 is dependent on the current fill state of the reservoir—that is, how much insulin is remaining in the reservoir. The position of the biasing member 23, and thus the base of the reservoir 27, is determined by the displacement sensor. The displacement sensor is therefore able to generate a signal indicative of the remaining quantity of insulin in the reservoir. By monitoring the change in the remaining quantity of insulin with respect to time, an actual rate of insulin delivery can be determined. This can be used by the control circuitry to apply corrections to the actual delivery rate by adapting the amount and/or timing of electrical current to the pumping device. The quantity of insulin remaining in the reservoir is transmitted to the handset 3, where it can be displayed to the patient and used as an indicator of when the patient should change the current cartridge for a new cartridge. The control circuitry in the body 21 may also transmit an indication of current battery level to the handset, so that the patient is made aware of when the battery requires recharging.

The delivery device also contains an activity monitor to track exercise (not shown). Exercise can have a significant effect on the amount of insulin needed for good control, so tracking exercise accurately is an important part of effective diabetes management. The activity monitor uses a sensor in the delivery device to detect movement of the delivery device, which can be used to infer when the user is engaged in physical activity. The detected activity is then wirelessly communicated to the handset via the wireless connection 5, where the handset (and the server) is able to track and record the patient's activity. Through an online portal to the server, the patient and permitted medical professionals are able to compare activity peaks with blood glucose to identify how activity is influencing the patient's need for insulin. This can in turn be used to program the handset with appropriate dosages for the patient.

Due to the fact that the patient interfaces with the handset rather than the delivery device itself, the delivery device is able to be made small and discreet, and is provided without buttons or a physical connection to a control unit.

Handset

Figure 3:
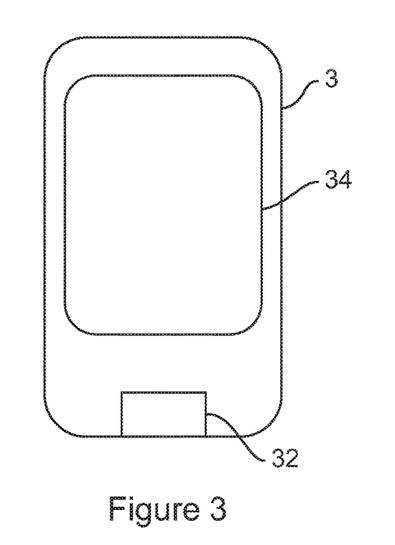
FIG. 3 shows a schematic view of a handset for controlling the drug delivery device of FIG. 2.

The handset 3 comprises two transceivers. The first transceiver is for communicating with the delivery device via the first wireless connection 5, while the second transceiver is for communicating with the server 4 via the second wireless connection 6. The handset also comprises a processor for running control software. The control software monitors the patient's condition and reports it to the central server 4, and controls the delivery of insulin doses to the patient by transmitting control signals to the delivery device 2. The handset 3 also comprises a touch screen display 34, which displays information to the user and provides a user interface for the user to input data, modify the basal rate, and trigger extraordinary bolas doses.

As well as wirelessly controlling the pump, the handset 3 also has an integral blood glucose meter 32. The blood glucose meter 32 detects the amount of glucose in the patient's blood. The blood may be analysed at the meter 32 by pricking the patient's finger and depositing a droplet of blood on a slide, which is inserted into the meter 32. The detected blood glucose level can be brought to the attention of the patient on the handset 3, and the patient can decide to trigger a bolas dose based on the blood glucose information. The result of every blood glucose test is automatically logged by the software and becomes immediately available for reference via the server 4 to the patient, medical professionals and even family members (such as parents). More generally, the handset 3 runs various software applications which help the user (and other authorised parties) to keep track of diet, insulin, blood glucose and exercise (which as explained above is recorded automatically from a sensor in the delivery device). By automating data collection, the handset 3 eliminates, or at least reduces, the need for a diabetes journal and ensures that comprehensive and accurate clinical information are constantly available to the patient and medical professionals via the server 4.

When controlling the delivery device, the handset 3 sends wireless signals to the delivery device 2 to deliver regular periodic doses of insulin at a pre-determined basal rate, which is set on the handset 3 according to the recommendations of a medical professional. The basal rate may be adjustable by the user within certain constraints. However, the software is configured such that it is not allowed for the basal rate to be adjusted remotely by third parties such as doctors. The hand-held device 3 also allows the user to trigger extraordinary bolus doses, for example after eating carbohydrates or performing exercise. As with a basal dose, the bolus dose is delivered by the delivery device 2 in response to control signals sent wirelessly from the handset 3. The user is able to input the volume of carbohydrates which have been consumed at a relevant time and is also able to input periods of exercise and the hand-held device is able to recommend adjustments to the basal rate or when a bolus is needed. As discussed above, the glucose monitor 32 may have an influence on the dosage. All of this information is transmitted to the server 4. The hand-held device 3 also receives information from the delivery device 2, for example to indicate whether it is faulty or when the insulin cartridge needs to be replaced. It also provides an indication of battery level.

Server

It will be understood from the above that the handset 3 and the delivery device 2 monitor and record clinical information while delivering insulin according to the body's needs. By providing this information to the server 4, it can be made almost immediately available to all those who need to see it. In particular, a mobile connection to a secure online management portal makes it possible for patients, clinicians and parents to be made constantly aware of, and able to react to, changing conditions. A diabetes clinic with patients using the system is able to see the current status of all its patients on a single screen, delivered to the clinic in real time. The portal can be accessed over the Internet in the clinic or through a smartphone. In addition to making it possible for a patient to access their latest clinical information online, it is possible for the patient to see simple visual analysis of their data, for example to identify trends and patterns in their blood sugar, and to immediately see their insulin dosing habits. This information can all be viewed using a simple online web portal that can be accessed from home, from work or from a smartphone. The server can also transmit SMS messages to a child's parents to let them know their child's information and state of health.

A patient using the system is provided with a personal login to the secure mobile diabetes management portal. Once logged in the patient can see all of their automatically collected data in the form of charts and graphs to help them understand where they might need to make adjustments. Exercise habits are mapped out in pie charts. An indication of exactly how and when the patient's insulin was delivered is provided. The patient's clinicians are able to see the same analysis and information, enabling them to call or text the patient whenever needed with guidance and advice.

From a single online dashboard screen, the clinic has access to the status of all the patients on the system; including current blood sugar, average blood sugar, insulin dosing, hypo frequency and blood testing habits. At a glance, anyone having difficulties can easily be identified for an immediate response. With a single click, all the data for a patient is analysed and charted to identify trends, patterns and problems. Using the portal, clinics can completely reorganise the way in which patients are managed. Text and email can be used to check on recent events. Clinic visits are focused completely on current and accurate information.

Managing Communications Between the Handset Device and the Server

As discussed above, the handset, as well as controlling the pump, also gathers information from the pump (including information from the activity monitor, a log of the basal and bolus doses administered, and other information regarding the state of the pump), as well as blood glucose readings from the blood glucose meter, and information manually entered by the user (e.g. carbohydrate input, or activity in the event that the activity monitor is not being used, or is not present). This information is transmitted by the handset via WiFi/3G to the secure server. The hand held device may for example use a GPRS machine to machine wireless data connection to communicate with the secure server to which it pushes the information, some of which relates to the patient's medical condition. One problem is that some countries or regions require that medical records for residents of that country be kept only in that country or region. For example, an EU directive is in place requiring that patient data for EU residents must not be stored outside of the EU. Even within a country, it is possible that several distributors could supply the product. In the event of a problem, a patient would need to be directed to the most appropriate customer care contact point. These are significant issues where a global server is used for administering handset devices worldwide. To address some of these issues, local databases are provided in individual countries or regionals for storing patient information, but there is some difficulty in routing information from a handset device to the appropriate local database in a secure and reliable manner. Moreover, at the time of manufacture, the identity of the end user, their country of residence and the contact details necessary for them to seek local support are all unknown.

To address this problem, when a handset is primed for delivery to a user, the IMEI (International Mobile Station Equipment Identity—a unique identifier for the handset) and handset serial number is stored in a database. This can occur at the point of manufacture, or just before dispatch to a user. Before using the handset, the user is required to activate it.

At first activation by the user, the user enters the serial number on an activation web page—accessed via a personal computer, mobile telephone or the like (but not the handset), and also selects his or her language and country or residence. A code is generated based on the IMEI corresponding to the serial number (for example the last 5 digits of the IMEI), the selected language and the selected country. The code is provided to the user (via the website). The user then enters the code into their handset. Then, every time the handset transmits data to the server, it includes the code—enabling the server to know where the data needs to be directed (e.g. to a database in a particular country). In this way, patient specific contact information is dynamically assigning to a handset, which will ensure that the user is connected to their home medical data server and which ensures that their handset displays appropriate contact information for support. A specific patient's profile is held on a global server, which in turn holds the IP address of the medical database server appropriate for their location, as well as contact details for their support (e.g. phone number, and web address). When a subscriber receives a new handset, they register the handset by entering, into the handset, a code which is generated by the global server. On connecting to the network, the handset initially connects to the global server from which it requests the IP address of the medical server and the customer support contact string. It then drops the connection to the global server and reattaches to the appropriate medical data server whereupon the medical data is uploaded. The support information for display on the handset is also updated.

Figure 4:
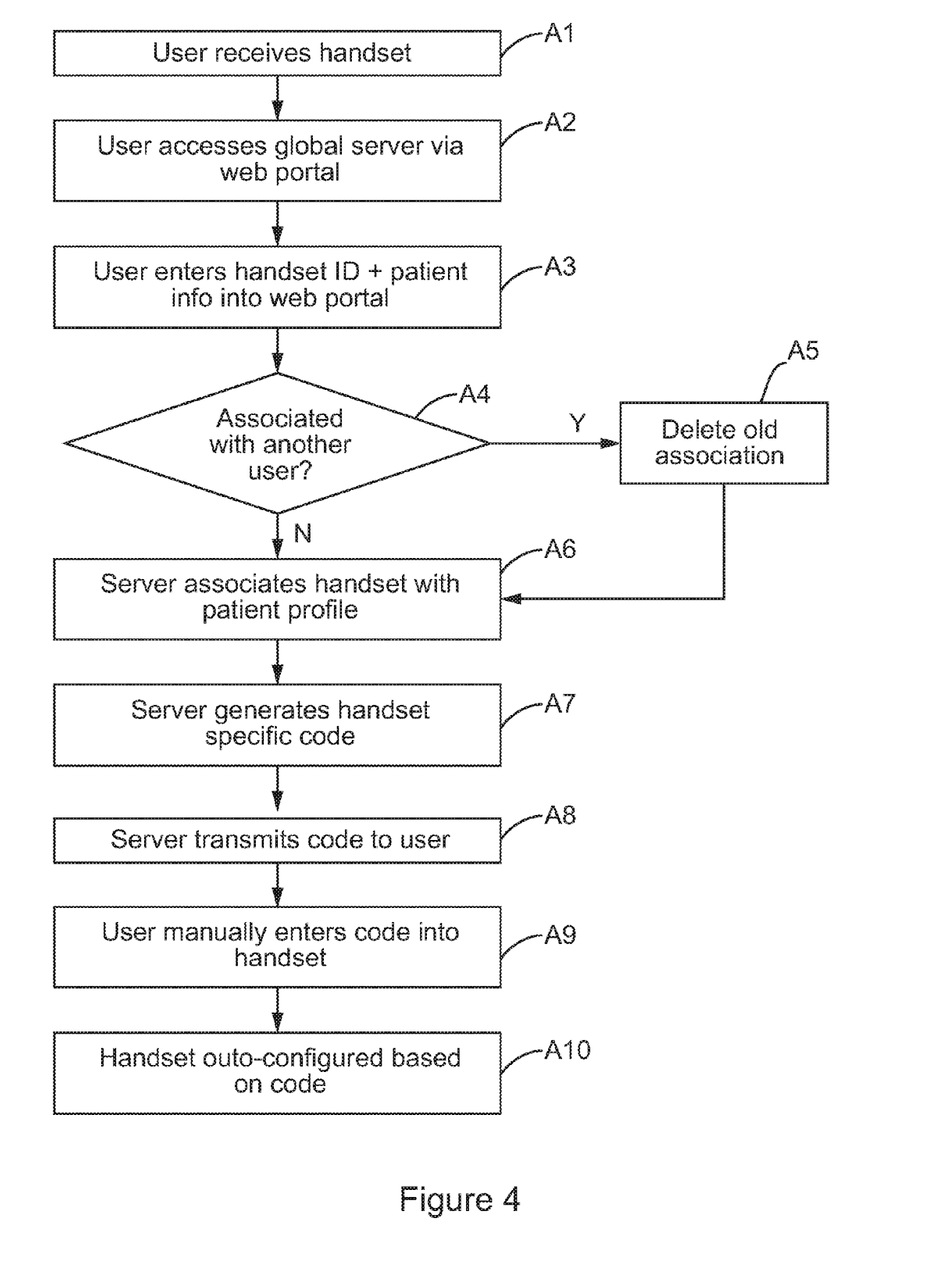
FIG. 4 is a schematic flow diagram of a method of registering a handset to a user.

Referring to FIG. 4, a method of registering a handset to a user is schematically illustrated. At a step A1, the user receives the handset, for example by post. Prior to delivery, the handset details have been stored in advance at a global server. At a step A2, the user accesses the global server via a web portal. For a new user, this may require the formation of a new patient profile. For an existing user, this may simply require a log in using a username and password. At a step A3, the user enters via the web portal a handset identification number (for example a serial number printed on the handset), as well as patient information (such as their country of residence and preferred language). At a step A4 the global server determines, from the identification number, whether the specific handset is currently associated with another user. If so, at a step A5 the association with the old user is deleted. The patient information associated with the old user need not be deleted—only the link between that patient information and the handset. At a step A6, the global server associated the handset with the patient profile of the new user. Then, at a step A7, the global server generates a handset specific code, based for example on part of an IMEI which corresponds to the handset identification number. The handset specific code is transmitted/provided to the user (via the web portal) at a step A8. At a step A9, the user enters the handset specific code into the handset. Future communications (see FIG. 5 below) will then include the handset specific code to facilitate routing. At a step A10, the handset may be auto-configured based on the code. For example, measurement units can be configured (e.g. between imperial and metric) based on country.

Figure 5:
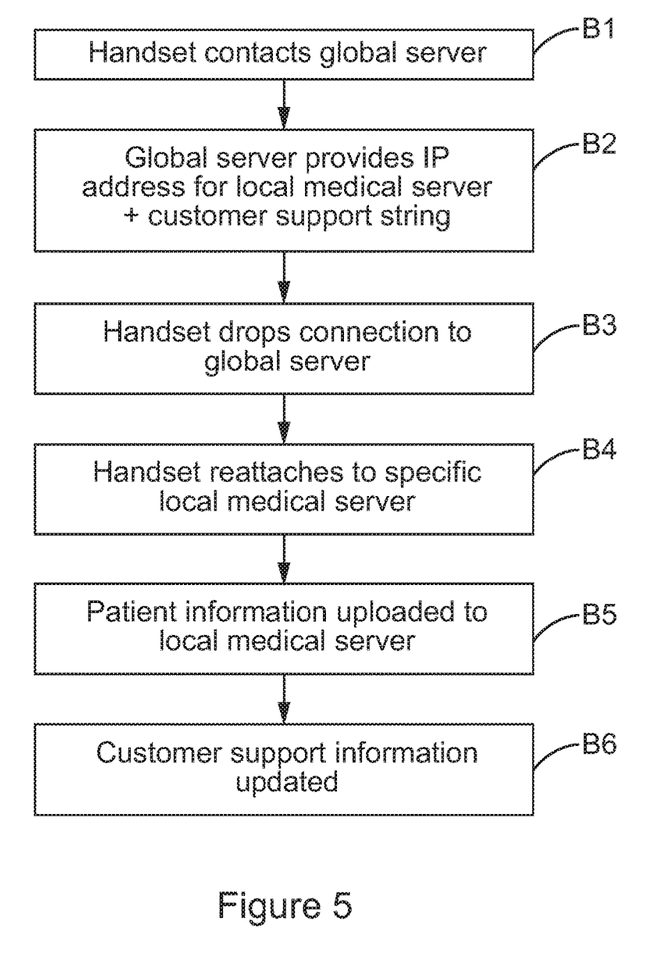
FIG. 5 is a schematic flow diagram of a method of routing communications to a local medical database.

FIG. 5 schematically illustrates the routing of communications to a local medical database. When medical data is to be transmitted to a server for storage in association with a user profile, at a step B1 the handset contacts the global server, identifying itself using the handset specific code. At a step B2, the global server provides an IP address for a local medical server to which the handset should provide the medical data. The global server also provides the handset with a current customer support string, which includes telephone, website and other contact details for local support in the country or region of the user. At this point, at a step B3, the handset drops the connection to the global server, and at a step B4 reattaches to the local medical server indicated by the global server, using the specified IP address. At a step B5, the handset uploads the patient data/medical information to the local medical server. The medical data may include the activity of the therapeutic product delivery device (therapeutic settings, such as insulin to carb ratios, insulin to blood glucose settings, maximum basal rate/bolus rate, or an indication of patient activity based on the activity monitor), carbohydrate input information (input by the user into the handset) or blood glucose readings (manually entered into the handset or determined from an integrated meter in the handset). The customer support information on the handset is also updated at a step B6—based on the customer support string provided by the global server. In this way, the handset is regularly updated with the current support information. This may also be used to notify the handset (and thus the user) of important information—for example software updates or service announcements.

Due to privacy issues surrounding medical data, it is important that a patient is able to explicitly grant/withdraw their consent for their data to be transferred and/or stored according to any legislation that applies. Further, it is important that the integrity of the data can be guaranteed, and associated with the correct individual. There is no guarantee that wireless coverage can be relied upon, and there may be cases in which the handset and the secure server states and associations could become misaligned, especially where wireless communication is unavailable at the time that a change is made. For example, the handset may be the property of a health care facility, which from time to time may reassign it. When this occurs, it is important that the data on the handset is cleared prior to reassignment, and that patient data on the secure server relates only to the intended patient and not to a subsequent or previous user of the handset. Also, a patient may choose to opt into data services, but then subsequently exercise their right to opt out. In order to address these issues, a method has been devised for managing the association of a portable wireless medical device with a specific patient, at a specific level of service using centrally generated tokens which avoid the unsafe states occurring especially where wireless coverage is unreliable. Functionality relating to a specific patient's profile is managed by the patient by means of a web browser which provides access to the secure server. The patient is able to accept or decline different levels of service including, but not limited to, no service, local device management only, device management with data connectivity and storage. For example, a user may be willing to send performance data (such as a number of good readings from blood glucose, or number of alarms) and ordering data (e.g. that a cartridge is running low, which could be used to trigger automatic ordering of a new cartridge for the patient) but not therapeutic information relating to their health. Other users might not want to send activity data (the amount of exercise they have undertaken, as tracked by the activity monitor. The patient enters the handset serial number and agrees to the terms and conditions associated with their choice. In response, the secure server generates a handset specific token which the user enters manually into the device. The server immediately assumes the requested state (e.g. accepts data, does not accept data). The handset is a slave and assumes the requested state on entry of the token (e.g. sends data, does not send data). Where a device is to be reassigned to a new user, an un-assign token is generated in relation to the old user, and is provided to the old user. As soon as this is generated, no further data will be accepted from the handset to which it applies. When the old user enters the token to handset, all values will assume factory default settings and all patient data in the handset will be erased (it will be appreciated that a copy of this information may still be retained at a server in association with the patient profile of the old user). No further data will be accepted from this handset until it has been reactivated (as described above in relation to FIG. 4) within the context of a specific subscriber. The server is considered to be the master, holding the state of the mobile device and enforcing limitations on the data that is stored and or used. The device is advised of this state asynchronously, by manual entry of a token.

Figure 6:
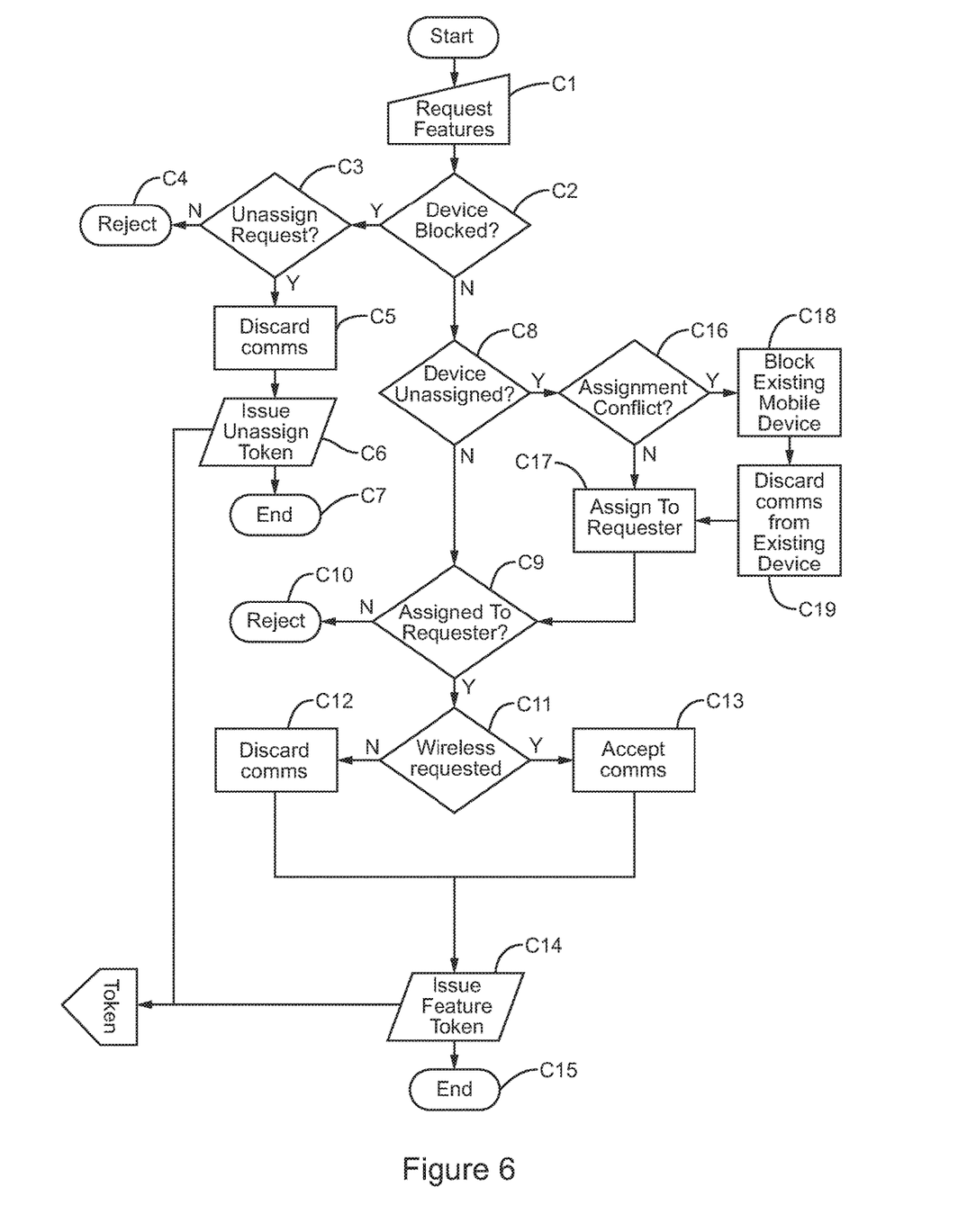
FIG. 6 is a schematic flow diagram of a method of generation of a token at a server.

FIG. 6 schematically illustrates the generation of a token at the server. At a step C1, the server receives a change request from the user of a handset. The change request may be received via the web portal. The request may relate to a number of possible changes, as will be discussed below. At a step C2, it is determined whether the handset to which the request relates is blocked. If so, then at a step C3 it is determined whether the change request is an unassign request to remove the association between the handset and a user to which the handset is currently assigned. If not, then the change request is rejected at a step C4 (because no other request is available in relation to a blocked handset). If the change request is an unassign request, then at a step C5 the server configures itself to reject future communications from the handset (until a new user is assigned to it as per FIG. 4), and then at a step C6 an unassign token is issued to the user via the web portal. At a step C7 the process then ends.

If at the step C2 it is determined by the server that the handset device is not blocked, then at a step C8 it is determined whether the device is currently assigned, or is not currently assigned to a user. If the handset device is already assigned to a user, then at a step C9 it is determined whether the user which the device is assigned to is the user making the change request. If not, then the change request is rejected at a step C10. If the device is currently assigned to the user making the change request, then it is determined at a step C11 whether the change request is for wireless transmission of medical data from the handset to the server to be active or inactive. If wireless transmission is requested, then at a step C13 the server will configure itself to accept medical data from the handset, and then at a step C14 the server will generate and issue to the user a feature token for entry into the handset. The process then ends at a step C15. If at the step C11 it is determined that wireless transmission from the handset to the server is to be inactive, then at a step C12 the server configures itself to discard any received communications from the handset (at least in relation to medical data, and in some cases in relation to all data), and then to generate a features token at the step C14 for entry into the handset. The process then ends at the step C15.

If at the step C8 it is determined that the handset is not currently assigned to a user, then at a step C16 it is determined whether there is an assignment conflict. This occurs if the user is already associated with another handset. In the case that there is no conflict, then at a step C17 the handset is associated with the requesting user, and the process rejoins the step C9 (and subsequent steps) to set whether or not the handset should communicate medical data to the server. If at the step C16 it is determined that there is a conflict, then at a step C18 the existing device associated with the requesting user is blocked, and any communications from the now blocked existing device are discarded by the server at a step C19. The new handset is then assigned to the requesting user at the step C17.

Figure 7:
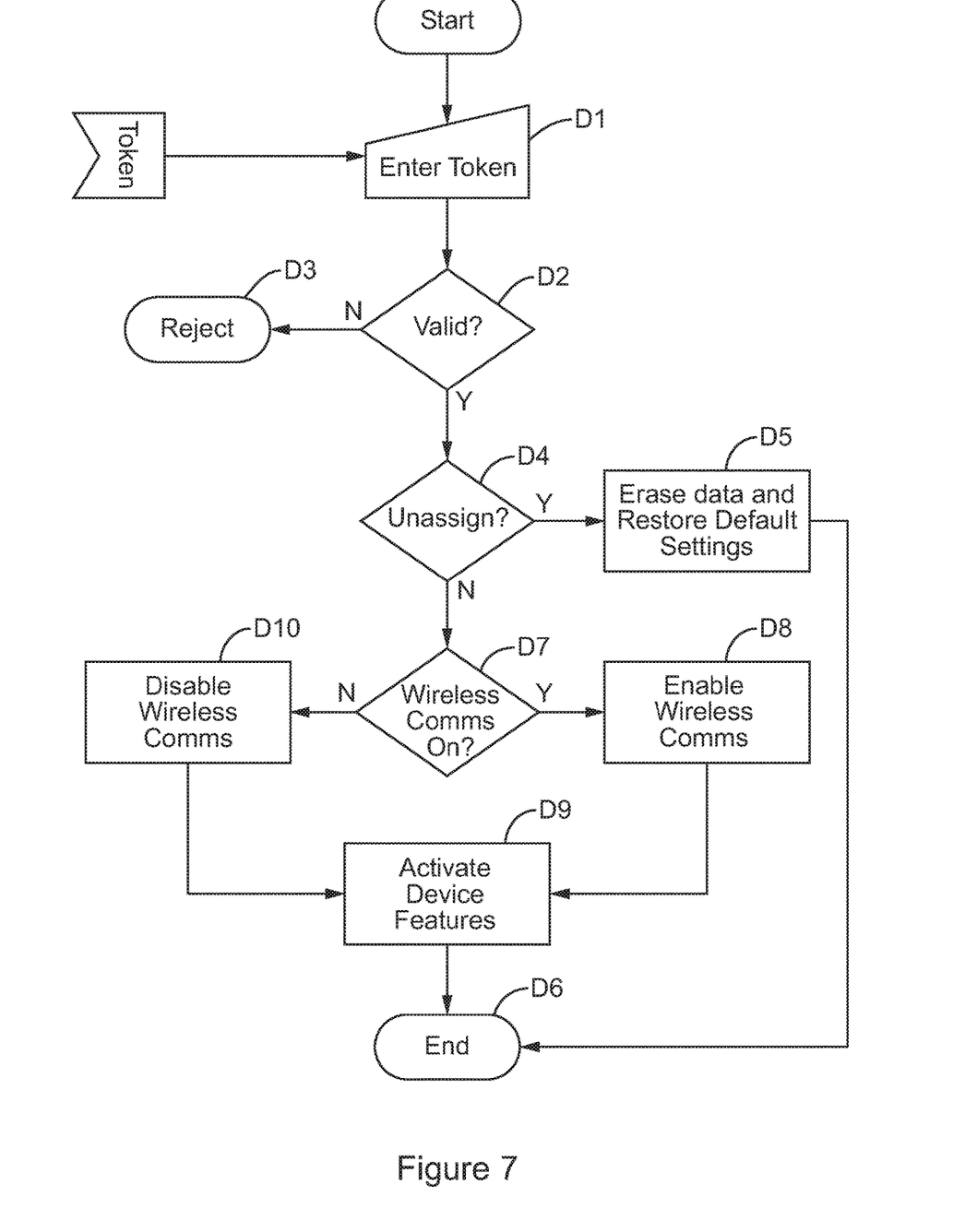
FIG. 7 is a schematic flow diagram of a chain of events which occurs when the user of the handset enters (manually) into the handset a token received from the server.

FIG. 7 schematically illustrates a chain of events which occurs when the user of the handset enters (manually) into the handset a token received via the web portal. At a step D1, the user enters (e.g. types) the token code into the handset. At a step D2, the handset determines whether the token is valid. A token may be determined as invalid if, for example, it has fewer or a greater number of digits than expected, if it does not have the format expected (e.g. a particular combination and/or order of numbers and letters), or if the code as a whole, or a part of a code, has an alphanumeric value which is not permitted. Typically a token code will be found to be invalid if it has been inputted incorrectly by the user. If the code is found to be invalid, then at a step D3 it will be rejected. The user may then attempt to re-enter the code correctly. If the code is found to be valid at the step D2, then at a step D4 it will be determined whether the code is an unassign code. A code may determined to be an unassign code if it takes on a particular value or format. If the code is determined to be an unassign code at the step D4, then at a step D5 the handset will erase all its data (or at least the data relating to the current user), and restore its default settings. The default settings may for example relate to the measurement units used, preferences for communicating with the server, or display settings (e.g. brightness etc.). The process then ends at a step D6. If at the step D4 the code is determined not to be an unassign code, then it is assumed to be a code for changing the state of the handset between a state in which it wirelessly communicates medical data to the server, and a state in which it doesn't. If at the step D7 it is determined that the handset should communicate medical data to the server, then at a step D8 wireless communications are enabled, and medical data will be periodically synchronised to the server. If on the other hand it is determined at the step D7 that the handset should not communicate medical data to the server, then at a step D10 wireless communications are disabled, and medical data will not be synchronised to the server. At a step S9, the device features are activated, following which the process ends at the step D6.

While embodiments of the present invention have been described with reference to an insulin delivery system, it will be appreciated that the present invention may be applied instead to the delivery of other drugs.

The invention claimed is:

1. A communication method of managing communications to and from a handset device controlling a therapeutic product delivery device, wherein the method comprises the steps of:
   storing unique identifiers of respective handset devices in a database on a server;
   transmitting from a new user, to the server, at least part of a unique identifier for a handset device together with new user information regarding the new user to be associated with the new user;
   at the server, determining from the at least part of the unique identifier whether the handset device is previously associated with another user and deleting any such previous association;
   at the server associating the handset device with the new user information and generating a handset specific code based upon the at least part of the unique identifier and the new user information, and transmitting the handset specific code to the new user;
   at the handset device,
      collecting data relating to the new user;
      receiving a manual input of the handset specific code; and
      transmitting the collected data from the handset device to the server in association with the handset specific code.

2. The communication method according to claim 1, wherein the new user information comprises the new user's country of residence, and wherein the server is responsive to the receipt of the handset specific code to establish a routing to a medical data server associated with the new user's country of residence.

3. The communication method according to claim 2, wherein the routing is established by providing the handset device with the IP address of the medical data server, and wherein the handset device is operable to drop the connection to the server and reattach to the medical data server at the indicated IP address.

4. The communication method according to claim 2, wherein the handset device is operable to transmit medical data regarding the new user to the medical data server.

5. The communication method according to claim 2, wherein the server is responsive to the receipt of the handset specific code to provide customer support information to the handset device, the handset device being responsive to receipt of the customer support information to update the customer support information for display at the handset device.

6. The communication method according to claim 1, wherein the unique identifier is an International Mobile station Equipment Identity.

7. The communication method according to claim 4, wherein the medical data comprises one or more of the activity of or settings for the therapeutic product delivery device, carbohydrate input information and blood glucose readings.

8. The communication method according to claim 2, wherein the handset is automatically configured in dependence on the new user's country of residence.

9. The communication method according to claim 1, wherein the new user information comprises a medical facility, clinic, healthcare professional or medical insurance company the new user is associated with, and the handset device is automatically configured in dependence on the medical facility, clinic, healthcare professional or medical insurance company associated with the new user.

10. The communication method according to claim 1, wherein if the server identifies in response to the unique identifier that the handset device is already associated with the another user, the server is operable to cancel the association between the handset device and the another user.

11. The communication method according to claim 1, wherein the unique identifier for the handset device is pre-stored at the server in advance of the new user's information being transmitted to the server.

12. A system for managing communications to and from a handset device controlling a therapeutic product delivery device, the system comprising:
   a server,
      for storing unique identifiers of a plurality of handset devices,
      for receiving from a new user at least part of a unique identifier for a handset device together with new user information regarding the new user to be associated with the handset device,
      the server being operable to determine from said the at least part of the unique identifier whether the handset device is previously associated with another user and to delete any such previous association, the server then being operable to associate the handset device with the new user information and to generate a handset specific code based upon the at least part of the unique identifier and the new user information, and transmit the handset specific code to the new user; and a handset device, collecting data relating to the new user;

receiving a manual input of the handset specific code, and transmitting the collected data from the handset device to the server in association with the handset specific code.

13. The system according to claim 12, wherein the new user's information comprises the new user's country of residence, and wherein the server is responsive to the receipt of the handset specific code to establish a routing to a medical data server associated with the new user's country of residence.

* * * * *